(12) United States Patent
Emslander et al.

(10) Patent No.: US 10,687,588 B2
(45) Date of Patent: Jun. 23, 2020

(54) PRINTED COMPONENTS AND METHODS FOR MAKING THE SAME

(71) Applicant: 3M INNOVATIVE PROPERTIES COMPANY, St. Paul, MN (US)

(72) Inventors: Jeffrey O. Emslander, City of Grant, MN (US); Siegfried R. Gabriel, Dusseldorf (DE); Michael R. Gorman, Lake Elmo, MN (US); Tilo Remhof, Hilden (DE); Robert L. W. Smithson, Mahtomedi, MN (US); Hans-Gerd Vollmers, Cologne (DE)

(73) Assignee: 3M Innovative Properties Company, St. Paul, MN (US)

( * ) Notice: Subject to any disclaimer, the term of this patent is extended or adjusted under 35 U.S.C. 154(b) by 303 days.

(21) Appl. No.: 15/516,441

(22) PCT Filed: Oct. 22, 2015

(86) PCT No.: PCT/US2015/056889
§ 371 (c)(1),
(2) Date: Apr. 3, 2017

(87) PCT Pub. No.: WO2016/065134
PCT Pub. Date: Apr. 28, 2016

(65) Prior Publication Data
US 2018/0228253 A1 Aug. 16, 2018

Related U.S. Application Data

(60) Provisional application No. 62/067,095, filed on Oct. 22, 2014.

(51) Int. Cl.
*B32B 27/02* (2006.01)
*A44B 18/00* (2006.01)
(Continued)

(52) U.S. Cl.
CPC ........ *A44B 18/008* (2013.01); *A44B 18/0065* (2013.01); *A61F 13/625* (2013.01);
(Continued)

(58) Field of Classification Search
CPC ............ A44B 18/0065; A44B 18/0069; A44B 18/008; A61F 13/625; A61F 13/84;
(Continued)

(56) References Cited

U.S. PATENT DOCUMENTS 4,775,310 A 10/1988 Fischer
4,816,374 A 3/1989 Lecomte
(Continued)

FOREIGN PATENT DOCUMENTS

CA 2165379 6/1996
DE 19509505 1/1996
(Continued)

OTHER PUBLICATIONS

Polyethylene/ Polypropylene (PE/PP), Product Description of LCX135939, Laser Marking Master batch, RTP Co. Imagineering Plastics, Jun. 12, 2014, 1 page.
(Continued)

*Primary Examiner* — Lawrence D Ferguson

(57) ABSTRACT

The present invention relates to printed hook components for hook and loop mechanical fasteners, and other components such as on diaper chassis and other personal hygiene articles, and methods for making the same. The hook component comprises an organic polymer, a laser-sensitive agent, and a laser-induced print on the hook component created by the interaction of electromagnetic radiation with the laser-sensitive agent. The hook component can be used in a variety of applications, including mechanical fastening devices for personal hygiene articles such as diapers, adult incontinence pads, and medical gowns.

14 Claims, 4 Drawing Sheets

(51) Int. Cl.
*A61F 13/62* (2006.01)
*B41M 5/26* (2006.01)
*A61F 13/84* (2006.01)

(52) U.S. Cl.
CPC .......... *A61F 13/84* (2013.01); *A61F 13/8405* (2013.01); *B41M 5/267* (2013.01); *A44B 18/0069* (2013.01); *A61F 2013/8497* (2013.01)

(58) Field of Classification Search
CPC ........ A61F 13/8405; A61F 2013/8497; B41M 5/26; B32B 7/02
See application file for complete search history.

(56) References Cited

U.S. PATENT DOCUMENTS

| | | | |
|---|---|---|---|
| 4,894,060 | A | 1/1990 | Nestegard |
| 5,077,870 | A | 1/1992 | Melbye |
| 5,206,280 | A | 4/1993 | Williams |
| 5,256,231 | A | 10/1993 | Gorman |
| 5,843,547 | A | 12/1998 | Kulper |
| 6,000,106 | A | 12/1999 | Kampfer |
| 6,075,179 | A | 6/2000 | McCormack |
| 6,190,594 | B1 | 2/2001 | Gorman |
| 6,190,758 | B1 | 2/2001 | Stopper |
| 6,287,665 | B1 | 9/2001 | Hammer |
| 6,627,133 | B1 | 9/2003 | Tuma |
| 6,645,569 | B2 | 11/2003 | Cramer |
| 6,693,657 | B2 | 2/2004 | Carroll |
| 7,198,743 | B2 | 4/2007 | Tuma |
| 7,214,334 | B2 | 5/2007 | Jens |
| 7,541,088 | B2 | 6/2009 | Bennett |
| 8,771,919 | B2 | 7/2014 | Wu |
| 9,079,443 | B2 | 7/2015 | Pudleiner |
| 9,132,506 | B2 | 9/2015 | Smithson |
| 2007/0036939 | A1 | 2/2007 | Ferry (Hinton) |
| 2007/0173581 | A1 | 7/2007 | Hager |
| 2008/0076065 | A1 | 3/2008 | Bennett |
| 2011/0065576 | A1 | 3/2011 | Campbell |
| 2011/0151171 | A1 | 6/2011 | Biegler |
| 2011/0200801 | A1 | 8/2011 | Pudleiner |
| 2012/0213934 | A1 | 8/2012 | Biegler |
| 2012/0318454 | A1 | 12/2012 | Biegler |
| 2013/0188003 | A1 | 7/2013 | Thaker |
| 2016/0346895 | A1* | 12/2016 | Dorf ................. B24B 7/20 |

FOREIGN PATENT DOCUMENTS

| | | |
|---|---|---|
| DE | 19806230 | 8/1999 |
| DE | 102007034636 | 11/2007 |
| EP | 0329884 | 8/1989 |
| EP | 0341993 | 11/1989 |
| EP | 0447032 | 9/1991 |
| EP | 0539504 | 5/1993 |
| EP | 1035818 | 9/2000 |
| EP | 1377522 | 1/2004 |
| EP | 1905585 | 4/2008 |
| EP | 2725063 | 4/2014 |
| GB | 2168653 | 6/1986 |
| GB | 2215116 | 9/1989 |
| GB | 2234601 | 2/1991 |
| GB | 2352824 | 2/2001 |
| JP | 2008-246537 | 10/2008 |
| WO | WO 1995-34263 | 12/1995 |
| WO | WO 2001-09230 | 2/2001 |
| WO | WO 2004-080498 | 9/2004 |
| WO | WO 2007-023865 | 3/2007 |
| WO | WO 2009-018555 | 2/2009 |
| WO | WO 2009-104779 | 8/2009 |
| WO | WO 2011-026106 | 3/2011 |
| WO | WO 2011-103200 | 8/2011 |
| WO | WO 2012-112768 | 8/2012 |
| WO | WO 2012-121910 | 9/2012 |
| WO | WO 2016-065134 | 4/2016 |

OTHER PUBLICATIONS

International Search report for PCT International Application No. PCT/US2015/056889 dated Feb. 1, 2016, 5 pages.

* cited by examiner

PRINTED COMPONENTS AND METHODS FOR MAKING THE SAME

CROSS REFERENCE TO RELATED APPLICATIONS

This application is a national stage filing under 35 U.S.C. 371 of PCT/US2015/056889, filed Oct. 22, 2015, which claims the benefit of U.S. Provisional Application No. 62/067,095, filed Oct. 22, 2014, the disclosure of which is incorporated by reference in its/their entirety herein.

FIELD OF INVENTION

The present invention relates to printed hook components, such as the hook component for hook and loop mechanical fasteners, as well as other printed components of diaper chassis and other personal hygiene articles, and methods for making the same. The hook components can be used in a variety of applications, including fastening devices for personal hygiene articles such as diapers, adult incontinence pads, and medical gowns.

BACKGROUND

Currently, printed components such as, e.g., hook components for hook and loop fasteners, used on diapers and other personal hygiene articles are generally made by ink jet printing a design (or mark) onto the surface of the component. In the case of hook components made from clear materials, the design may be printed onto the back of the hook component and viewed through the surface opposite that which has been printed. In other cases, the design may be printed onto the surface containing the hook elements. In the former case, the hook component is limited to see-through materials. In the latter case, the design often lacks clarity due to the three dimensional nature of the hook elements. In both cases, the ink is applied to the surface of the hook component and can be rubbed off during use, thus affecting the durability and the quality of print.

SUMMARY

The present disclosure describes laser-induced printing of hook components of a hook and loop fastener, by the interaction of electromagnetic radiation with a corresponding laser-sensitive agent. Other components, such as on various locations on a diaper chassis and other personal hygiene articles, can also be printed according to the present disclosure. The print may include a track and trace number, a manufacturing code and/or date, a reference mark for alignment in a manufacturing process, a graphic image, or any other conceivable image or design. Such prints can be customizable, non-destructive, durable and sharp. Moreover, the prints may be applied to the hook component on the same time scale that many product manufacturing lines operate. This would allow an end product manufacturer, rather than the hook component manufacturer, to customize and carry out the actual printing in-line.

In one embodiment, the present disclosure provides an article comprising: a hook component of a hook-and-loop mechanical fastener, the hook component further comprising a first organic polymer and a first laser-sensitive agent; and a first laser-induced print on the hook component created by the interaction of electromagnetic radiation with the first laser-sensitive agent.

In another embodiment, the present disclosure provides a method comprising: providing a hook component of a hook-and-loop mechanical fastener, the hook component further comprising an organic polymer and a laser-sensitive agent, directing electromagnetic radiation onto the hook component to create a laser-induced print by the interaction of the electromagnetic radiation with the laser-sensitive agent.

In a further embodiment, the present disclosure provides an article comprising: a hook component of a hook-and-loop mechanical fastener, the hook component comprising a backing having a first side and a second side opposite the first side, and posts extending from the first side of the backing, wherein each post has a proximal end contiguous with the first side of the backing and a distal end opposite the proximal end; an adhesive on the second side of the backing; a release liner covering at least a portion of the adhesive, the release liner comprising an organic polymer and a laser-sensitive agent; and at least one laser-induced print on the release liner created by the interaction of electromagnetic radiation with the laser-sensitive agent.

In yet another embodiment, the present disclosure provides a method comprising: providing an article comprising a hook component of a hook-and-loop mechanical fastener, the hook component further comprising a backing having a first side and a second side opposite the first side, and posts extending from the first side of the backing, wherein each post has a proximal end contiguous with the first side of the backing and a distal end opposite the proximal end, an adhesive on the second side of the backing, a release liner covering at least a portion of the adhesive, the release liner further comprising an organic polymer and a laser-sensitive agent; and directing electromagnetic radiation onto the release liner to create a laser-induced print by the interaction of electromagnetic radiation with the laser-sensitive agent.

In another embodiment there is provided an article comprising a component comprising a first organic polymer and a first laser-sensitive agent; and a first laser-induced print on the component created by the interaction of electromagnetic radiation with the first laser-sensitive agent. The article may be a diaper and the component may, for example, be selected from a landing zone, a fastening tape, a diaper topsheet and a diaper backsheet. The component may comprise a film backing, a nonwoven fabric, a woven fabric and combinations of the aforementioned. Other articles include other personal hygiene articles such as, for example, adult incontinence pads and medical gowns.

As used herein, the terms "including," "comprising," or "having" and variations thereof encompass the items listed thereafter and equivalents thereof, as well as additional items. All numerical ranges are inclusive of their endpoints and non-integral values between the endpoints unless otherwise stated. Terms such "top," "bottom," "first side," "second side" and the like are used to describe elements as they relate to one another, but are in no way meant to recite specific orientations of an article or apparatus, to indicate or imply necessary or required orientations of an article or apparatus, or to specify how an article or apparatus described herein will be used, mounted, displayed, or positioned in use. Terms such as "first," "second," "third," etc. with respect to "organic polymer," "laser-sensitive agent," and "laser-induced print" are used only to describe separate entities, which may or may not be the same (e.g., a first organic polymer can be the same as a second organic polymer OR the first organic polymer can be different from the second organic polymer), and the presence of one entity does not necessarily imply the presence of another entity with a higher or lower number (e.g., a third laser-induced print can exist without a second laser-induced print).

The above summary of the present disclosure is not intended to describe each disclosed embodiment or every implementation of the present disclosure. The description that follows more particularly exemplifies illustrative embodiments. It is to be understood, therefore, that the drawings and following description are for illustrative purposes only and should not be read in a manner that would unduly limit the scope of this disclosure.

With reference to the figures, like reference numbers offset by multiples of 100 (e.g., 18, 118, 218) indicate like elements. Some elements may be present in similar or identical multiples; in such cases the elements may comprise the same reference number, with one or more of the elements designated by a prime (') for convenience of description. Unless otherwise indicated, all figures and drawings in this document are not to scale and are chosen for the purpose of illustrating different embodiments of the invention. In particular, the dimensions of the various components are depicted in illustrative terms only, and no relationship between the dimensions of the various components should be inferred from the drawings, unless so indicated.

DETAILED DESCRIPTION

Particularly preferred application of the present disclosure is for the hook components of hook and loop fasteners. It will be understood, however, that the present disclosure will be useful for components of various articles such as, e.g., printing on diaper attachment landing zones and other components of a diaper chassis and other personal hygiene articles.

Figure 1A:
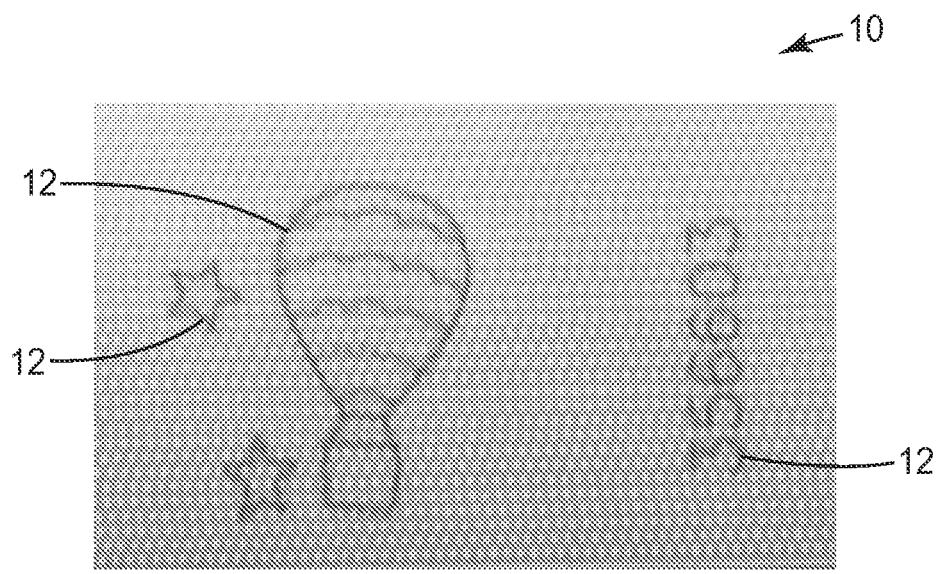
FIG. 1A is a photograph of one embodiment of an exemplary printed hook component of the present disclosure.
Figure 1B:
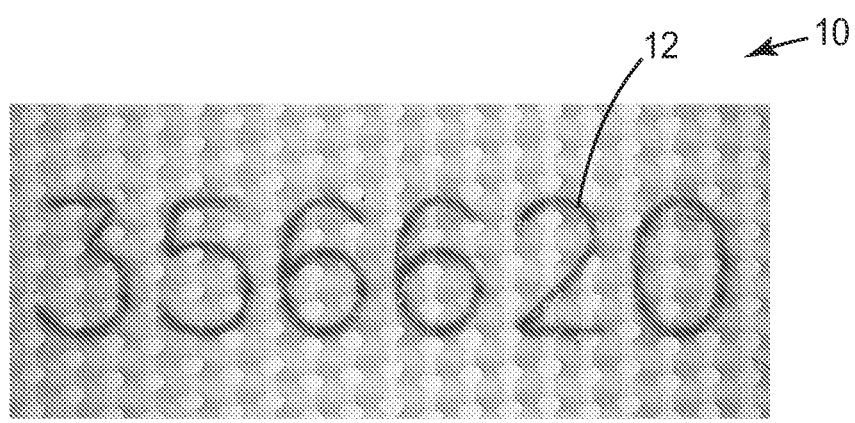
FIG. 1B is a photograph of an alternative embodiment of an exemplary printed hook component of the present disclosure.

Exemplary embodiments of printed hook components are illustrated in FIGS. 1A-1B. A hook component 10 comprises a first organic polymer and a first laser-sensitive agent. A first laser-induced print 12 on the hook component 10 is created by the interaction of electromagnetic radiation with the first laser-sensitive agent.

Figure 2:
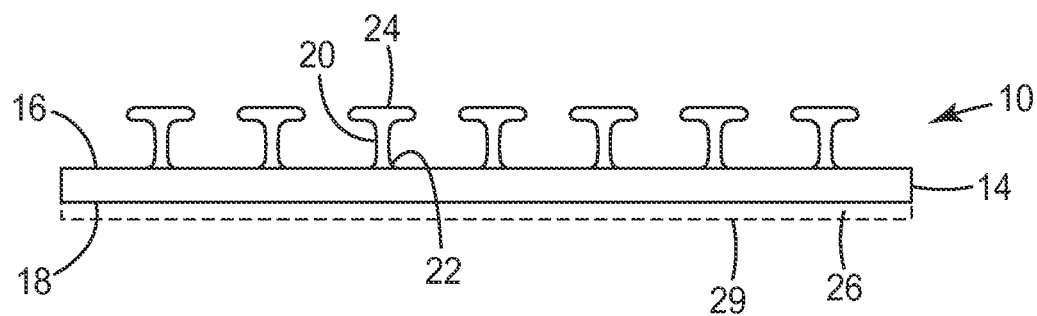
FIG. 2 is a schematic cross-sectional segment of an exemplary hook component.

As illustrated in FIG. 2, the hook component 10 may further comprise a backing 14 having a first side 16 and a second side 18 opposite the first side 16. Posts 20 extend from the first side 16 of the backing 14, such that each post 20 has a proximal end 22 contiguous with the first side 16 of the backing 14 and a distal end 24 opposite the proximal end 22. In some embodiments, posts may extend from both sides of the backing. Although the posts 20 in FIG. 2 are arranged perpendicular to the backing 14, the posts 20 could also be slanted at an angle to the backing 14 and still engage the loop component of a hook and loop mechanical fastener.

The distal end 24 of the post 20 is typically fashioned to enhance engagement with the loop component of a mechanical fastener. For example, the distal end 24 of at least some of the posts 20 may be formed into loop engaging heads having the shape of a mushroom (e.g., with a circular or oval head enlarged with respect to the post), a hook, a palm-tree, a nail, a T, a J or combinations thereof. The distal ends 24 of the posts 20 need not all be the same shape and/or orientation within a given hook component. For the purposes of this disclosure, the term "posts" will mean posts with or without loop-engaging heads, depending on the embodiment.

The hook component 10 shown in FIG. 2 has a continuous backing. However, it should be understood that the hook component may be slit (partially or completely through the backing), perforated, or reticulated (i.e. net-like) to impart, for example, breathability or flexibility to the hook component. Such properties may be particularly useful in the personal care industry where a high priority is placed on comfort.

Hook Component

The material composition of the hook component includes a first organic polymer and a first laser-sensitive agent. The first organic polymer is not particularly limiting, but typically comprises a thermoplastic polymer. Exemplary thermoplastic polymers include polyolefin homopolymers such as polyethylene, polypropylene, and polybutylene, copolymers of ethylene, propylene and/or butylenes, and copolymers and blends thereof; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. In some presently preferred embodiments, the thermoplastic is a polyolefin (e.g., polyethylene, polypropylene, polybutylene, ethylene copolymers, propylene copolymers, butylene copolymers, and copolymers and blends of these materials), a polyester and combinations thereof. Preferably, the thermoplastic is a polyolefin.

The first laser-sensitive agent is dispersed, substantially homogeneously, within the hook component and may be activated by electromagnetic radiation to form the first laser-induced print. Suitable first laser-sensitive agents include dyes, pigments and compounds containing one or more chromophores that interact with electromagnetic radiation in typically the 200-2000 nm range to produce a laser-induced print. In some embodiments, the electromagnetic radiation is in the 300-400 nm range. In other embodiments, the electromagnetic radiation is in the 1000-1100 nm range. First laser-sensitive agents may be organic materials, inorganic materials, or a combination thereof (e.g., metal ion complex with one or more organic moieties).

Exemplary inorganic first laser-sensitive agents include one or more metal oxides such as crystalline (e.g., rutile) titanium dioxide ($TiO_2$), tin oxide, indium tin oxide, and combinations thereof. In certain presently preferred embodiments, the first laser-sensitive agent comprises metal oxide particles selected from titanium dioxide, tin oxide, indium tin oxide, and combinations thereof. Preferably, the first laser-sensitive agent comprises titanium dioxide. Suitable commercially available sources of titanium dioxide include, for example, the titanium dioxides available from E. I. du Pont de Nemours and Company ("DuPont") in Wilmington, Del. under the "Ti-Pure" trademark, such as the product designated "Ti-Pure R-902+". Minor amounts of silica ($SiO_2$), alumina ($Al_2O_3$) and/or aluminum hydroxide may be present in the titanium dioxide. Typically, silica, alumina and/or aluminum hydroxide are present in the form of an outer coating that surrounds each particle of $TiO_2$.

Another exemplary first laser-sensitive agent is commercially available as LCS 135939 from RTP Company in Winona, Minnesota.

The amount of first laser-sensitive agent in the hook component is dictated by both performance and cost. Typically, the minimum amount is that amount which is sufficient to form a visible printing of the desired intensity. The maximum amount, in turn, is usually dictated by economics, where amounts over that necessary to produce print of the desired intensity are avoided.

In some embodiments, the first laser-sensitive agent is typically present at a concentration up to about 10% by weight, more particularly up to about 8% by weight, even more particularly up to about 4% by weight of the hook component. In some embodiments, the first laser-sensitive agent is about 0.4% to 8% by weight, more particularly about 0.4% to 2% by weight of the hook component.

The hook component may contain additional ingredients, depending upon the intended application of the mechanical fastener. Non-limiting examples of optional ingredients include adhesion promoters; biocides (antibacterials, fungicides, and mildewcides); anti-static agents; bonding, blowing and foaming agents; dispersants; fillers and extenders; smoke suppressants; impact modifiers; initiators; lubricants; micas; pigments, colorants and dyes; optical brighteners; plasticizers; processing aids; other polymers; release agents; slip and anti-blocking agents; stabilizers; viscosity regulators; waxes; and combinations thereof. Preferably, the optional ingredients have little or minimal interaction with the wavelength of electromagnetic radiation used to print the hook component.

Any number of current methods can be used to make the hook component. The hook component can be made, for example, by feeding a molten resin containing the first organic polymer, first laser-sensitive agent and any additional ingredients between a nip formed by two rolls or a nip formed between a die face and roll surface, with at least one of the rolls having cavities. The cavities may be the inverse shape of a post having a loop-engaging head or may be the inverse shape of a post without loop-engaging heads. Pressure provided by the nip forces the resin into the cavities. In some embodiments, a vacuum can be used to evacuate the cavities for easier filling. The nip is typically sufficiently wide such that a continuous backing is formed over the cavities. The mold surface and cavities can optionally be air or water cooled before stripping the integrally formed backing and posts from the mold, such as by a stripper roll. If the posts formed upon exiting the cavities do not have loop-engaging heads, loop-engaging heads can be subsequently formed into hooks by a capping method as described in U.S. Pat. No. 5,077,870 (Melbye et al.). Typically, the capping method includes deforming the tip portions of the hook elements using heat and/or pressure. The heat and pressure, if both are used, could be applied sequentially or simultaneously.

Other suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Still other suitable tool rolls may include wire-wrapped rolls, which are disclosed along with their method of manufacturing, for example, in U.S. Pat. No. 6,190,594 (Gorman et al.). Another exemplary method for forming a thermoplastic backing with posts includes using a flexible mold belt defining an array of post-shaped cavities as described in U.S. Pat. No. 7,214,334 (Jens et al.). Yet other useful methods for forming a thermoplastic backing with posts can be found in U.S. Pat. No. 6,287,665 (Hammer); U.S. Pat. No. 7,198,743 (Tuma); and U.S. Pat. No. 6,627,133 (Tuma).

Another useful method for forming posts (e.g., with loop-engaging heads) on a thermoplastic backing is profile extrusion described, for example, in U.S. Pat. No. 4,894,060 (Nestegard). Typically, in this method a thermoplastic flow stream is passed through a patterned die lip (e.g., cut by electron discharge machining) to form a web having ridges that extend in the machine direction, slicing the ridges in a direction perpendicular to the machine direction, and stretching the web in the machine direction to form separated projections. The ridges may form hook precursors and exhibit the cross-sectional shape of posts (e.g., with loop-engaging heads) to be formed. The thermoplastic backing of the hook component made by this method has stretch-induced molecular orientation.

In some embodiments of exemplary hook components, the thickness of the backing is up to about 400, 250, 150, 100, 75 or 50 micrometers, depending on the desired application. In some embodiments, the thickness of the backing ranges from about 30 to 225 micrometers, more particularly about 50 to 200 micrometers, or even more particularly about 100 to 150 micrometers. In some embodiments, the posts have a maximum height (above the backing) of up to about 3 mm, 1.5 mm, 1 mm, or 0.5 mm and, in some embodiments a minimum height of at least about 0.05 mm, 0.1 mm, or 0.2 mm. In some embodiments, the posts have an aspect ratio (that is, a ratio of height to width at the widest point) of at least about 2:1, 3:1, or 4:1.

Printing Hook Components

Generally, the method for printing the hook component comprises providing a hook component of a hook-and-loop mechanical fastener, where the hook component further comprises an organic polymer and a laser-sensitive agent. Electromagnetic radiation is directed onto the hook component to create a laser-induced print by the interaction of electromagnetic radiation with the laser-sensitive agent.

Figure 3:
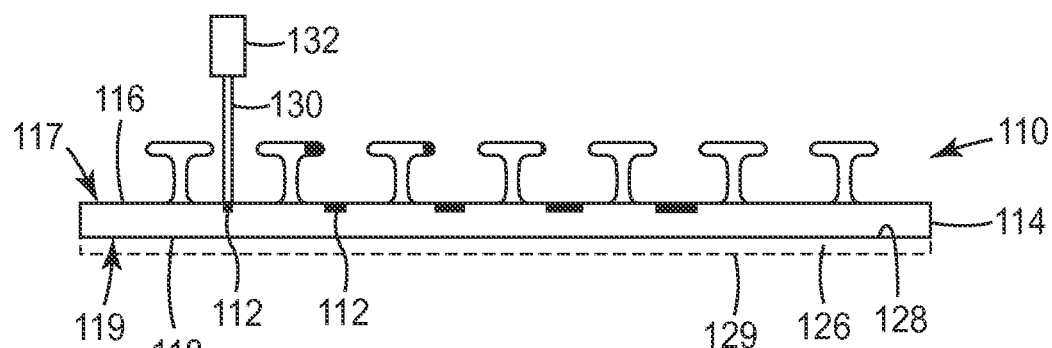
FIG. 3 is a schematic representation of an exemplary method for printing a hook component.

An exemplary method for printing the hook components is illustrated in FIG. 3. The hook component 110 comprises a first side 117 and a second side 119 opposite the first side 117. The hook component 110 containing a first organic polymer and a first laser-sensitive agent is typically provided as a continuous sheet or roll (e.g. a web). Alternatively, the hook component can be provided in discrete pieces. A beam 130 of electromagnetic radiation from a laser 132 is focused onto the first side 117 of the hook component 110 in the area to be printed. The type of laser and wavelength of electromagnetic radiation are properly selected to interact with the first laser-sensitive agent to create a laser-induced print 112. The laser-induced print 112 is typically darker in appearance than the surrounding portions of the hook component 110 that are not subject to the beam 130 of the electromagnetic radiation.

Only the area of hook component under the beam of electromagnetic radiation changes color, resulting in a very sharp, customizable image, even on the surface of the hook component containing the three-dimensional posts. Without wishing to be bound by theory, the print is believed to derive from a photochemical activation of the laser-sensitive agent, as well as a thermal reaction with the first organic polymer in the immediate vicinity of the exposed laser-sensitive agent. Because the print arises from the transformation of materials making up the hook component, the print is essentially embedded within the hook component, making it more durable and permanent than current ink jet printing methods.

Preferably, the laser parameters are selected to minimize any thermal effects that might cause degradation of the hook component and, consequently, loss of functionality. Therefore, it is preferable to use electromagnetic radiation having a wavelength from 200-2000 nm, which corresponds to the ultraviolet (UV), visible, and near infrared (IR) regions of the electromagnetic spectrum. Preferably, UV electromagnetic radiation is used.

For hook samples containing titanium dioxide, the activation wavelength is typically in the range of 300-400 nm, more particularly in the range of 350-360 nm. Applicable lasers include a Nd:YAG laser that has been frequency-tripled to achieve a wavelength of 355 nm and a Nd:YdO$_4$ diode pumped solid state laser. The energy of the electromagnetic radiation may be up to about 300, 100, 60, or 50 microJoules. In some embodiments, the energy of the electromagnetic radiation may range from about 10-300 microJoules, more particularly from about 10-100 microJoules, and even more particularly from about 30-60 microJoules.

The pulsing width of the laser may be up to about 200 ns, 100 ns or 60 ns. In some embodiments, the pulsing width ranges from about 1-200 ns, more particularly from about 10-100 ns, and even more particularly from about 30-60 ns. The repetition rate of the laser may be up to about 250 kHz or 150 kHz. In some embodiments, the repetition rate is about 10-250 kHz, more particularly about 70-150 kHz.

Printing with UV and near IR electromagnetic radiation is demonstrated in Examples 1-3, as provided herein.

Although FIG. 3 shows the laser-induced print 112 on the first side 117 of hook component, the laser-induced print 112 could be applied to the second side 119 of the hook component 110 by, for example, flipping the hook component 110 so that the second side 119 faces the laser 132 or, alternatively, simply repositioning the laser.

Figure 4:
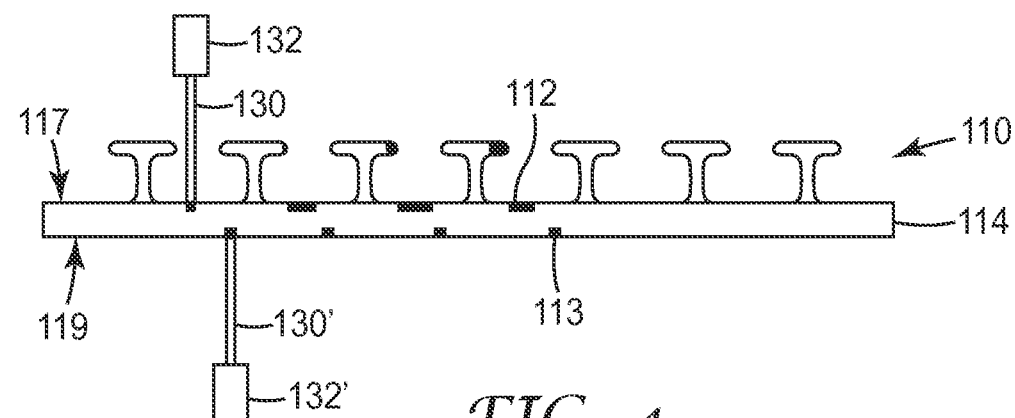
FIG. 4 is a schematic representation of another exemplary method for printing a hook component.

In some embodiments, laser-induced print is provided on both sides of the hook component 110. FIG. 4 illustrates one method for making such a printed hook component. A beam 130 of electromagnetic radiation from a laser 132 is focused onto the first side 117 of the hook component 110 in the area to be printed. Similarly, a beam 130' of electromagnetic radiation from a laser 132' is focused onto the second side 119 of the hook component. In some embodiments, the first laser-induced print may be the same as the second laser-induced print. In other embodiments, the first laser-induced print may be different from the second laser-induced print. The prints on each side may be aligned directly over each other, off-set from each other, or a combination thereof.

Hook Component Laminates

In some embodiments, the second side of the backing 18, 118 may be laminated to a carrier 26, 126, as illustrated in FIGS. 2-3. Although in FIGS. 2-3, the carrier 26, 126 and backing 14, 114 have the same planar dimensions, this need not necessarily be so. In some embodiments, for example, the carrier may extend beyond at least one of the backing's planar dimensions. Similarly, although the hook components 10, 110 in FIGS. 2-3 have a continuous backing 14, 114, this need not be the case. In some embodiments, the backing could be discontinuous, e.g., slit, slit and spread (to create apertures), perforated, or reticulated.

The carrier may also be continuous or discontinuous (e.g. slit, perforated, reticulated). The carrier may comprise a variety of suitable materials including woven webs, nonwoven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof. In some embodiments, the carrier is a fibrous material (e.g., a woven, nonwoven, or knit material). In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. In other embodiments, the carrier may not contain individual layers but the material content varies through the thickness of the carrier. In yet other embodiments, the carrier may be a composite web comprising a nonwoven layer and a dense film layer.

Useful carriers may have any suitable basis weight or thickness that is desired for a particular application. For a fibrous carrier, the basis weight may range, e.g., from at least about 5, 8, 10, 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

The hook component may be laminated to the carrier by a variety of processes including, but not limited to, adhesive bonding, thermal bonding, point bonding, ultrasonic welding and combinations thereof. Suitable adhesives include water-based, solvent-based, pressure-sensitive, and hot-melt adhesives. Suitable thermal bonding techniques include those disclosed in U.S. Pat. Appl. Pub. No. 2011/0151171 (Biegler et al.), U.S. Pat. Appl. Pub. No. 2012/0318454 (Biegler et al.), and U.S. Pat. Appl. Pub. No. 2012/0213934 (Biegler et al.). Each of these processes is well-known to those skilled in the art.

Printing Hook Component Laminates

In some embodiments, the carrier is printable using the same laser-induced print method described above for the hook component. In such cases, the carrier comprises a second organic polymer, a second laser-sensitive agent, and a third laser-induced print created by the interaction of electromagnetic radiation with the second laser-sensitive agent. The second organic polymer may be the same or different from the first organic polymer, and the second laser-sensitive agent may be the same or different from the first laser-sensitive agent. In some preferred embodiments, the first and second laser-sensitive agents are the same material.

Referring to FIG. 3, the carrier 126 may be printed on the second side 129 of the carrier 126 with a second laser (not shown) positioned underneath the carrier 126. Alternatively, in cases where the backing 114 of the hook component 110 is discontinuous (e.g., slit and spread, perforated or reticulated) such that the first side 128 of the carrier is visible through the discontinuities in the backing 114, printing may occur on the first side 128 of the carrier 126 employing the same or different laser used to print the first side 116 of the backing 114. An example of such a laminate in which the first sides of both the backing and carrier are printed is described in Example 2 and shown in FIG. 6. In some embodiments, laser-induced prints may be applied to both the first and second sides 128, 129 of the carrier 126.

Adhesive with Release Layer

There are a number of applications in which it would advantageous to provide a roll (or pieces) of hook component or laminate that may be adhesively applied to a substrate by an end user. Therefore, in some embodiments, an adhesive is applied to the second side 29 of the carrier 26 illustrated in FIG. 2 or, in the absence of a carrier 26, to the second side 18 of the backing 114. A release liner at least partially covers the adhesive to prevent contamination prior to use. When ready to apply the hook component to a substrate, the user simply removes the release liner to expose the adhesive and applies the hook component adhesive-side down to the substrate.

The adhesive is typically a pressure-sensitive adhesive. Pressure-sensitive adhesives suitable for this invention include tackified rubber adhesives, such as natural rubber, olefins, silicones, polyisoprene, polybutadiene, polyurethanes, SIS and SBS block copolymers, and other elastomers, and tackified or untackified acrylic adhesives such as copolymers of isooctylacrylate and acrylic acid, which can be polymerized by radiation, solution, suspension, or emulsion techniques.

The pressure-sensitive adhesive can be applied to the backing by a variety of known methods. For example, the pressure sensitive adhesive can either be directly coated onto the backing, or formed as a separate layer and then later laminated to the backing. As another example, the pressure-sensitive adhesive could be coated onto a release layer and then adhesively coupled to the backing. The adhesive may be applied to the backing continuously or discontinuously.

To improve adhesion of the pressure-sensitive adhesive, the backing can optionally be pretreated prior to the coating of the laminating step by corona discharge, plasma discharge, flame treatment, electron beam irradiation, ultraviolet radiation, and/or chemical priming.

Any conventional release liner may be used. Exemplary release liners include olefins (e.g., polyethylene and polypropylene) and coated papers (e.g., silicone coated papers). However, in some cases it may be advantageous to print the release liner, as well as the hook component. Therefore, in some embodiments, the release liner comprises a third organic polymer, a third laser-sensitive agent, and a fourth laser-induced print created by the interaction of electromagnetic radiation with the third laser-sensitive agent. The third organic polymer may be the same or different from either the first or second organic polymer. Similarly, the third laser-sensitive agent may be the same or different from the first or second laser-sensitive agent. The fourth laser-induced print may be the same or different from the first laser-induced print on the backing of the hook component. In other embodiments, the release liner does not contain a laser-induced print.

Figure 6:
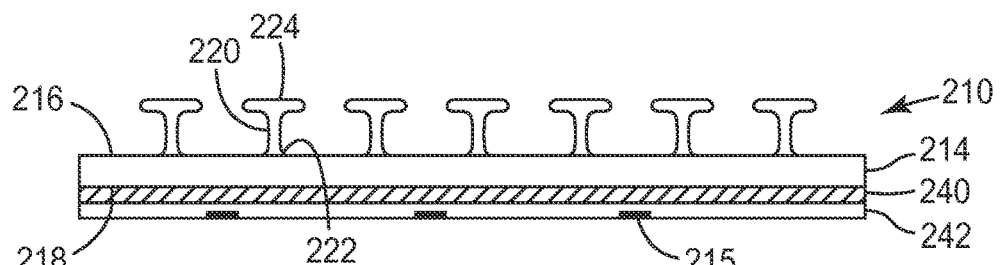
FIG. 6 is a schematic cross-sectional segment of an exemplary hook component with printed release liner.

FIG. 6 illustrates an alternative embodiment of the present disclosure where only the release liner is printed. The article represented in FIG. 6 includes a hook component 210 of a hook-and-loop mechanical fastener. The hook component 210 comprises a backing 214 having a first side 216 and a second side 218 opposite the first side 216. Posts 220 extend from the first side 216 of the backing 214, where each post 220 has a proximal end 222 contiguous with the first side 216 of the backing 214 and a distal end 224 opposite the proximal end 222. An adhesive 240 is applied to the second side 218 of the backing 214. The adhesive 240 may be applied continuously or discontinuously. A release liner 242 covers at least a portion of the adhesive 240. The release liner 242 comprises an organic polymer and a laser-sensitive agent. At least one laser-induced print 215 is created by the interaction of electromagnetic radiation with the laser-sensitive agent.

Hook and Loop Mechanical Fasteners

The hook component of the present disclosure is combined with a loop component to form a hook and loop mechanical fastener. The posts of the hook component will reversibly engage with the loop component to create the mechanical fastener. In some embodiments, the mechanical fastener is self-contained. For example, with reference to FIG. 2, the carrier 26 may be a loop component that engages with the distal end 24 of the posts 20 when the hook component 10 is circled back onto itself (e.g., tying a bundle of cords together). In other embodiments, the loop component and hook component can be physically separated from each (e.g., fastening a hook component on the tab of a diaper to a loop component on the front of a diaper to secure the diaper about the waist of the user).

The term loop component, as used herein, refers to any material that can reversibly engage with the hook component. In some embodiments, the loop components comprise fibrous loops which engage with the posts on the hook component. In other embodiments, the loop components do not actually comprise loops but provide structure that can catch and engage with the posts of the hook component.

The loop components are typically formed from knitted fabrics, woven fabrics, or non-woven fabrics (e.g., spunbond webs, spunlaced webs, airlaid webs, meltblown web, and bonded carded webs). For example, the mechanical fasteners may include fiber loops projecting from a knitted, woven, or non-woven backing or may be extrusion-bonded, adhesive-bonded, and/or sonically-bonded fiber loops. Useful loop materials may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

In some embodiments, the loop material comprises a fibrous layer disposed on a substrate. Suitable substrates include textiles, paper, thermoplastic films (e.g., single- or multilayered films, coextruded films, laterally laminated films, or films comprising foam layers), and combinations thereof. The thickness of the substrate may be up to about 400, 250, 150, 100, 75 or 50 micrometers, depending on the desired application. In some embodiments, the thickness of the substrate is in a range from 30 to about 225 micrometers, from about 50 to about 200 micrometers, or from about 100 to about 150 micrometers.

Exemplary suitable loop components are described, for example, in U.S. Pat. No. 5,256,231 (Gorman et al.) and U.S. Pat. No. 5,389,416 (Mody et al.). As described in U.S. Pat. No. 5,256,231 (Gorman et al.), the fibrous layer in a loop material according to some embodiments disclosed herein comprises arcuate portions projecting in the same direction from spaced anchor portions on the backing.

Suitable commercially available mechanical loop materials include knitted and extrusion-bonded loop materials from 3M Company, St. Paul, Minn.

Applications for Hook and Loop Mechanical Fasteners

The printed hook components disclosed herein may be used in any application where hook and loop fasteners may be used. One exemplary application includes absorbent articles in the personal hygiene industry. Such articles typically comprise a liquid permeable topsheet, a liquid impermeable backsheet, and an absorbent core enclosed therebetween.

The liquid permeable topsheet can consist of a nonwoven material, e.g., spunbonded, meltblown, carded, hydroentangled, and wetlaid. Suitable nonwoven materials can be composed of natural fibers, such as woodpulp or cotton fibers, manmade fibers, such as polyester, polyethylene, polypropylene, viscose, or from a mixture of natural and manmade fibers. The topsheet material may further be composed of tow fibers, which may be bonded to each other in a bonding pattern, as, e.g., disclosed in EP-A-1 035 818. Further examples of topsheet materials are porous foams, apertured plastic films, etc. The materials suitable as topsheet materials should be soft and non-irritating to the skin and be readily penetrated by urine.

The liquid impermeable backsheet may consist of a thin plastic film, e.g., a polyethylene or polypropylene film, a nonwoven material coated with a liquid impervious material, a hydrophobic nonwoven material which resists liquid penetration, or laminates of plastic films and nonwoven materials. The backsheet material may be breathable so as to allow vapour to escape from the absorbent core, while still preventing liquids from passing through the backsheet material.

The topsheet and the backsheet material typically extend beyond the absorbent core and are connected to each other, e.g., by gluing or welding by heat or ultrasonic, about the periphery of the absorbent core. The topsheet and/or the backsheet may further be attached to the absorbent core by any method known in the art, such as adhesive, heatbonding etc. The absorbent core may also be unattached to the topsheet and/or the backsheet.

The absorbent body can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. It is also common to have absorbent bodies comprising layers of different material with different properties with respect to liquid receiving capacity, liquid distribution capacity and storage capacity. The thin absorbent bodies often comprise a compressed mixed or layered structure of cellulosic fluff pulp and superabsorbent.

The hook component typically forms part of a fastening tab and is bonded to at least one of the front waist region or the rear waist region. The fastening tab may extend outwardly from at least one of the left longitudinal edge or the right longitudinal edge of the absorbent article. In other embodiments, the hook component may be an integral ear portion of the absorbent article.

Figure 7:
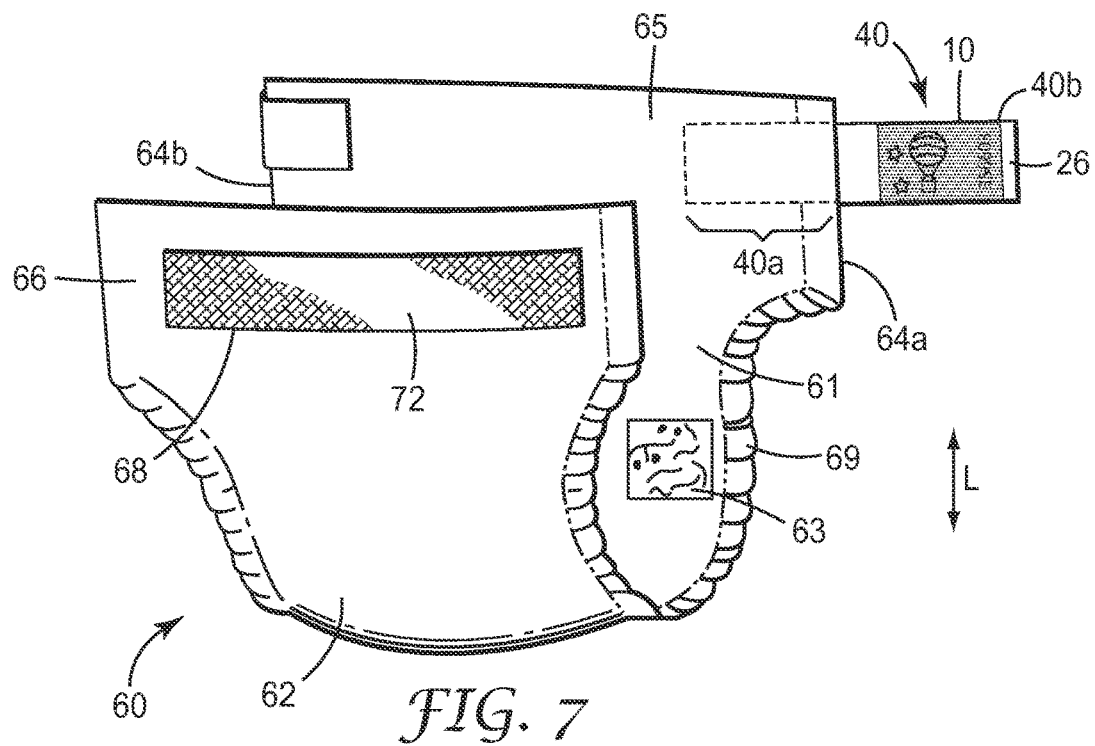
FIG. 7 is an exemplary absorbent article comprising the printed hook component in FIG. 1A.
Figure 8:
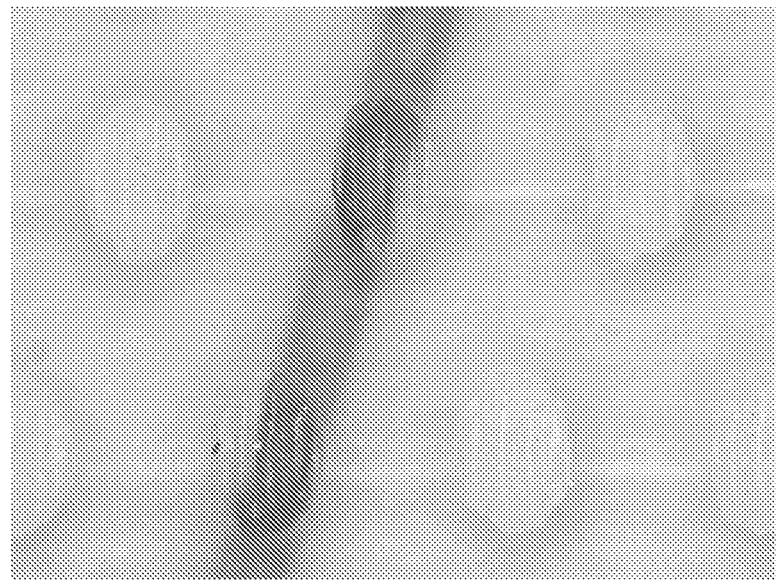
FIG. 8 is a close-up photograph of a printed hook component.

FIG. 7 is a schematic perspective view of one exemplary embodiment of an absorbent article. The absorbent article is a diaper 60 having an essentially hourglass shape. The diaper comprises an absorbent core 63 between a liquid permeable top sheet 61 that contacts the wearer's skin and an outwardly facing liquid impermeable back sheet 62. Diaper 60 has a rear waist region 65 having two fastening tabs 40 arranged at the two longitudinal edges 64a, 64b of diaper 60 and extending beyond longitudinal edges 64a, 64b of the diaper 60. The diaper 60 may comprise an elastic material 69 along at least a portion of longitudinal side edges 64a and 64b to provide leg cuffs. The longitudinal direction "L" of the absorbent article (e.g., diaper 60) refers to the direction that the article extends from the front to rear of the user. Therefore, the longitudinal direction refers to the length of the absorbent article between the rear waist region 65 and the front waist region 66. The lateral direction of the absorbent article (e.g., diaper 60) refers to the direction that the article extends from the left side to the right side (or vice versa) of the user (i.e., from longitudinal edge 64a to longitudinal edge 64b in the embodiment of FIG. 7).

Fastening tab 40 usually extends beyond longitudinal edges 64a, 64b of the diaper 60. The manufacturer's end 40a corresponds to the part of fastening tab 40 which is fixed or secured to the diaper 60 during the manufacture of the diaper 60. The user's end is typically gripped by the user when attaching the diaper 60 to the wearer and is typically not fixed to the diaper during manufacturing.

In FIG. 7, fastening tabs 40 are secured through their manufacturer's end 40a to the rear waist region 65. The user's end 40b of the fastening tab 40 comprises a hook component according to the present disclosure. The configuration of the hook component 10 is shown and described above in FIG. 1A. In some embodiments, when attaching the diaper 60 to a wearer's body, the user's ends 40b of fastening tabs 40 can be attached to a target area 68 comprising a loop component 72 which may be arranged on the back sheet 62 of the front waist region 66. Examples of materials that can be used as loop components are described above and disclosed, for example, in U.S. Pat. No. 5,389,416 (Mody et al.) EP 0,341,993 (Gorman et al.) and EP 0,539,504 (Becker et al.). In other embodiments, the back sheet 62 comprises a woven or nonwoven fibrous layer which serves as a loop component by interacting with the user's ends 40b of fastening tabs 40 comprising a hook component disclosed herein. Examples of such back sheets 62 are disclosed, for example, in U.S. Pat. No. 6,190,758 (Stopper) and U.S. Pat. No. 6,075,179 (McCormack et al.).

Although the embodiment illustrated in FIG. 7 is an absorbent article with attached fastening tabs, it is envisioned that the mechanical fastener disclosed herein would be equally useful in absorbent articles with larger areas of hooks. For example, the ears of the absorbent article themselves comprise hooks, or the absorbent article can have two target zones of loop material along the longitudinal edges of the back sheet in one waist region and two hook strips extending along the longitudinal edges of the absorbent article in the opposite waist region.

The articles according to and/or made according to the present disclosure may also be useful in many other fastening applications, for example, assembly of automotive parts or any other application in which reversible attachment may be desirable.

Some Embodiments of the Disclosure

In a first embodiment, the present disclosure provides an article comprising: a hook component of a hook-and-loop mechanical fastener, the hook component comprising a first organic polymer and a first laser-sensitive agent; and a first laser-induced print on the hook component created by the interaction of electromagnetic radiation with the first laser-sensitive agent.

In a second embodiment, the present disclosure provides the article of the first embodiment, wherein the first organic polymer is a thermoplastic polymer.

In a third embodiment, the present disclosure provides the article of the first or second embodiment, wherein the first organic polymer is selected from the group consisting of a polyolefin, a polyester, a polyamide, a polyurethane, a polycarbonate, a poly(vinyl alcohol), a ketone, a polyphenylene sulfide, and combinations thereof.

In a fourth embodiment, the present disclosure provides the article of any one of the first to third embodiments, wherein the first organic polymer is selected from the group consisting of a polyolefin, a polyester, and combinations thereof.

In a fifth embodiment, the present disclosure provides the article of any one of the first to fourth embodiments, wherein the first organic polymer is a polyolefin.

In a sixth embodiment, the present disclosure provides the article of any one of the first to fifth embodiments, wherein the hook component further comprises at least one of adhesion promoters; biocides; anti-static agents; bonding, blowing and foaming agents; dispersants; fillers and extenders; smoke suppressants; impact modifiers; initiators; lubricants; micas; pigments, colorants and dyes; optical brighteners; plasticizers; processing aids; other polymers; release agents; slip and anti-blocking agents; stabilizers; viscosity regulators; waxes; and combinations thereof.

In a seventh embodiment, the present disclosure provides the article of any one of the first to sixth embodiments, wherein the first laser-sensitive agent is a metal oxide.

In an eighth embodiment, the present disclosure provides the article of any one of the first to seventh embodiments, wherein the first laser-sensitive agent is selected from the group consisting of crystalline titanium dioxide, tin oxide, indium tin oxide, zinc oxide, and combinations thereof.

In a ninth embodiment, the present disclosure provides the article of any one of the first to eighth embodiments, wherein the first laser-sensitive agent is 0.4% to 8% by weight of the hook component.

In a tenth embodiment, the present disclosure provides the article of any one of the first to ninth embodiments, wherein the first laser-sensitive agent is 0.4% to 2% by weight of the hook component.

In an eleventh embodiment, the present disclosure provides the article of any one of the first to tenth embodiments, wherein the first laser-induced print comprises at least one of a graphic image, a fiducial mark and a track-and-trace number.

In a twelfth embodiment, the present disclosure provides the article of any one of the first to eleventh embodiments, wherein the hook component is selected from the group consisting of slit, perforated, reticulated, and combinations thereof.

In a thirteenth embodiment, the present disclosure provides the article of any one of the first to twelfth embodiments, wherein the hook component comprises a backing having a first side and a second side opposite the first side, and posts extending from the first side of the backing, wherein each post has a proximal end contiguous with the first side of the backing and a distal end opposite the proximal end.

In a fourteenth embodiment, the present disclosure provides the article of the thirteenth embodiment, wherein the distal end of at least some of the posts have shapes selected from the group consisting of mushroom, hook, palm-tree, nail, T, J, and combinations thereof.

In a fifteenth embodiment, the present disclosure provides the article of any one of the first to fourteenth embodiments, wherein the hook component has a first side and a second side opposite the first side, and the first laser-induced print is located on either the first or second side of the hook component.

In a sixteenth embodiment, the present disclosure provides the article of the fifteenth embodiment, further comprising a second laser induced print on the side of the hook component opposite the side containing the first laser-induced print.

In a seventeenth embodiment, the present disclosure provides the article of any one of the thirteenth to sixteenth embodiments, further comprising a carrier laminated to the second side of the backing.

In an eighteenth embodiment, the present disclosure provides the article of the seventeenth embodiment, wherein the carrier comprises at least one of woven webs, non-woven webs, textiles and plastic films.

In a nineteenth embodiment, the present disclosure provides the article of the seventeenth or eighteenth embodiment, wherein the carrier is laminated to the second side of the backing using at least one of adhesive bonding, thermal bonding, point bonding and ultrasonic welding.

In the twentieth embodiment, the present disclosure provides the article of any one of the seventeenth to nineteenth embodiments, wherein the carrier comprises a second organic polymer, a second laser-sensitive agent, and a third laser-induced print created by the interaction of electromagnetic radiation with the second laser-sensitive agent.

In a twenty-first embodiment, the present disclosure provides the article of the twentieth embodiment, wherein the second organic polymer is different from the first organic polymer.

In a twenty-second embodiment, the present disclosure provides the article of any one of the thirteenth to sixteenth embodiments, further comprising an adhesive on the second side of the backing and a release liner to cover the adhesive.

In a twenty-third embodiment, the present disclosure provides the article of the twenty-second embodiment, wherein the release liner comprises a third organic polymer, a third laser-sensitive agent, and a fourth laser-induced print created by the interaction of electromagnetic radiation with the third laser-sensitive agent.

In a twenty-fourth embodiment, the present disclosure provides a mechanical fastener comprising the article of any one of the first to twenty-third embodiments.

In a twenty-fifth embodiment, the present disclosure provides a personal hygiene product comprising the article of any one of the first to twenty-third embodiments.

In a twenty-sixth embodiment, the present disclosure provides an article comprising: a hook component of a hook-and-loop mechanical fastener, the hook component comprising a backing having a first side and a second side opposite the first side, and posts extending from the first side of the backing, wherein each post has a proximal end contiguous with the first side of the backing and a distal end opposite the proximal end; an adhesive on the second side of the backing; a release liner covering at least a portion of the adhesive, the release liner comprising an organic polymer and a laser-sensitive agent; and at least one laser-induced print on the release liner created by the interaction of electromagnetic radiation with the laser-sensitive agent.

In a twenty-seventh embodiment, the present disclosure provides the article of the twenty-sixth embodiment, wherein the laser-sensitive agent is a metal oxide.

In a twenty-eighth embodiment, the present disclosure provides the article of the twenty-sixth or twenty seventh embodiment, wherein the laser-sensitive agent is selected from the group consisting of crystalline titanium dioxide, tin oxide, indium tin oxide, zinc oxide, and combinations thereof.

In a twenty-ninth embodiment, the present disclosure provides the article of any one of the twenty-sixth to twenty-eighth embodiments, wherein the laser-sensitive agent is 0.4% to 8% by weight of the hook component.

In a thirtieth embodiment, the present disclosure provides the article of any one of the twenty-sixth to twenty-ninth embodiments, wherein the laser-sensitive agent is 0.4% to 2% by weight of the hook component.

In a thirty-first embodiment, the present disclosure provides the article of any one of the twenty-sixth to thirtieth embodiments, wherein the laser-induced print comprises at least one of a graphic image, a fiducial mark and a track-and-trace number.

In a thirty-second embodiment, the present disclosure provides the article of any one of the twenty-sixth to thirty-first embodiments, wherein the hook component is selected from the group consisting of slit, perforated, reticulated, and combinations thereof.

In a thirty-third embodiment, the present disclosure provides the article of any one of the twenty-sixth to thirty-second embodiments, wherein the distal end of at least some of the posts have shapes selected from the group consisting of mushroom, hook, palm-tree, nail, T, J, and combinations thereof.

In a thirty-fourth embodiment, the present disclosure provides a method comprising: providing a hook component of a hook-and-loop mechanical fastener, the hook component comprising an organic polymer and a laser-sensitive agent, directing electromagnetic radiation onto the hook component to create a laser-induced print by the interaction of the electromagnetic radiation with the laser-sensitive agent.

In a thirty-fifth embodiment, the present disclosure provides the method of the thirty-fourth embodiment, wherein electromagnetic radiation has a wavelength ranging from 200-2000 nm.

In a thirty-sixth embodiment, the present disclosure provide the method of the thirty-fourth or thirty-fifth embodiment, wherein the electromagnetic radiation has a wavelength ranging from 1000-1100 nm.

In a thirty-seventh embodiment, the present disclosure provides the method of the thirty-fourth or thirty-fifth embodiment, wherein the electromagnetic radiation has a wavelength ranging from 300-400 nm.

In a thirty-eighth embodiment, the present disclosure provides the method of any one of the thirty-fourth to thirty-seventh embodiments, wherein the electromagnetic radiation has a pulse duration of 1-200 ns.

In a thirty-ninth embodiment, the present disclosure provides the method of any one of the thirty-fourth to thirty-eighth embodiments, wherein the electromagnetic radiation has a pulse duration of 10-100 ns.

In a fortieth embodiment, the present disclosure provides the method of any one of the thirty-fourth to thirty-ninth embodiments, wherein the electromagnetic radiation has a pulsing width ranging from 10-250 kHz.

In a forty-first embodiment, the present disclosure provides the method of any one of the thirty-fourth to fortieth embodiments, wherein the electromagnetic radiation has a pulsing width ranging from 70-150 kHz.

In a forty-second embodiment, the present disclosure provides the method of any one of the thirty-fourth to forty-first embodiments, wherein the organic polymer is a thermoplastic polymer.

In a forty-third embodiment, the present disclosure provides the method of any one of the thirty-fourth to forty-second embodiments, wherein the organic polymer is selected from the group consisting of a polyolefin, a polyester, a polyamide, a polyurethane, a polycarbonate, a poly (vinyl alcohol), a ketone, a polyphenylene sulfide, and combinations thereof.

In a forty-fourth embodiment, the present disclosure provides the method of any one of the thirty-fourth to forty-third embodiments, wherein the organic polymer is selected from the group consisting of a polyolefin, a polyester, and combinations thereof.

In a forty-fifth embodiment, the present disclosure provides the method of any one of the thirty-fourth to forty-fourth embodiments, wherein the organic polymer is a polyolefin.

In a forty-sixth embodiment, the present disclosure provides the method of any one of the thirty-fourth to forty-fifth embodiments, wherein the hook component further comprises at least one of adhesion promoters; biocides; antistatic agents; bonding, blowing and foaming agents; dispersants; fillers and extenders; smoke suppressants; impact modifiers; initiators; lubricants; micas; pigments, colorants and dyes; optical brighteners; plasticizers; processing aids; other polymers; release agents; slip and anti-blocking agents; stabilizers; viscosity regulators; waxes; and combinations thereof.

In a forty-seventh embodiment, the present disclosure provides the method of any one of the thirty-fourth to forty-sixth embodiments, wherein the laser-sensitive agent is a metal oxide.

In a forty-eighth embodiment, the present disclosure provides the method of any one of the thirty-fourth to forty-seventh embodiments, wherein the laser-sensitive agent is selected from the group consisting of crystalline titanium dioxide, tin oxide, indium tin oxide, zinc oxide, and combinations thereof.

In a forty-ninth embodiment, the present disclosure provides the method of any one of the thirty-fourth to forty-eighth embodiments, wherein the laser-sensitive agent is 0.4% to 8% by weight of the hook component.

In a fiftieth embodiment, the present disclosure provides the method of any one of the thirty-fourth to forty-ninth embodiments, wherein the laser-sensitive agent is 0.4% to 2% by weight of the hook component.

In a fifty-first embodiment, the present disclosure provides the method of any one of the thirty-fourth to fiftieth embodiments, wherein the laser-induced print comprises at least one of a graphic image, a fiducial mark and a track-and-trace number.

In a fifty-second embodiment, the present disclosure provides a method comprising: providing an article comprising a hook component of a hook-and-loop mechanical fastener, the hook component further comprising a backing having a first side and a second side opposite the first side, and posts extending from the first side of the backing, wherein each post has a proximal end contiguous with the first side of the backing and a distal end opposite the proximal end, an adhesive on the second side of the backing, a release liner covering at least a portion of the adhesive, the release liner further comprising an organic polymer and a laser-sensitive agent; and directing electromagnetic radiation onto the release liner to create a laser-induced print by the interaction of electromagnetic radiation with the laser-sensitive agent.

In a fifty-third embodiment, the present disclosure provides the method of the fifty-second embodiment, wherein the electromagnetic radiation has a wavelength ranging from 200-2000 nm.

In a fifty-fourth embodiment, the present disclosure provides the method of the fifty-second or fifty-third embodiment, wherein the electromagnetic radiation has a wavelength ranging from 1000-1100 nm.

In a fifty-fifth embodiment, the present disclosure provides the method of the fifty-second or fifty-third embodiment, wherein the electromagnetic radiation has a wavelength ranging from 300-400 nm.

In a fifty-sixth embodiment, the present disclosure provides the method of any one of the fifty-second to fifty-fifth embodiments, wherein the electromagnetic radiation has a pulse duration of 1-200 ns.

In a fifty-seventh embodiment, the present disclosure provides the method of any one of the fifty-second to fifty-sixth embodiments, wherein the electromagnetic radiation has a pulse duration of 10-100 ns.

In a fifty-eighth embodiment, the present disclosure provides the method of any one of the fifty-second to fifty-seventh embodiments, wherein the electromagnetic radiation has a pulse width ranging from 10-250 kHz.

In a fifty-ninth embodiment, the present disclosure provides the method of any one of the fifty-second to fifty-eighth embodiments, wherein the electromagnetic radiation has a pulse width ranging from 70-150 kHz.

In a sixtieth embodiment, the present disclosure provides the method of any one of the fifty-second to fifty-ninth embodiments, wherein the organic polymer is selected from the group consisting of a polyolefin, a polyester, and combinations thereof.

In a sixty-first embodiment, the present disclosure provides the method of any one of the fifty-second to sixtieth embodiments, wherein the organic polymer is a polyolefin.

In a sixty-second embodiment, the present disclosure provides the method of any one of the fifty-second to sixty-first embodiments, wherein the laser-sensitive agent is a metal oxide.

In a sixty-third embodiment, the present disclosure provides the method of any one of the fifty-second to sixty-second embodiments, wherein the laser-sensitive agent is selected from the group consisting of crystalline titanium dioxide, tin oxide, indium tin oxide, zinc oxide, and combinations thereof.

In a sixty-fourth embodiment, the present disclosure provides the method of any one of the fifty-second to sixty-third embodiments, wherein the laser-sensitive agent is 0.4% to 8% by weight of the hook component.

In a sixty-fifth embodiment, the present disclosure provides the method of any one of the fifty-second to sixty-fourth embodiments, wherein the laser-sensitive agent is 0.4% to 2% by weight of the hook component.

In a sixty-sixth embodiment, the present disclosure provides the method of any one of the fifty-second to sixty-fifth embodiments, wherein the laser-induced print comprises at least one of a graphic image, a fiducial mark and a track-and-trace number.

EXAMPLES

The following examples are presented to illustrate some of the advantages of the loop components of the present disclosure and are not intended in any way to otherwise limit the scope of the invention.

Example 1

Example 1 was a hook component obtained from 3M Company, St. Paul, Minn., under the trade designation CS600 (of the general type described in U.S. Pat. No. 6,000,106). The hook component was composed of 98.5% Dow C700-35N copolymer (Dow Chemical Company, Midland, Mich.) and 1.5% (w/w) of a white color master batch (White 1015100S, 50% TiO2, 50% 30 melt flow index polypropylene copolymer, Clariant Masterbatches, Minneapolis, Minn.). The post density was approximately 1,600/square inch. The posts were approximately 380 microns tall with generally disc-shaped heads at the ends distal from the backing. The component was approximately 100 microns thick (not counting the height of the posts). The backing and posts were of integral construction. The hook component was marked with a 355 nm laser (Coherent Avia 355-3000, Coherent, Inc. Santa Clara, Calif.). The pulse width of the laser was approximately 40 ns and typical pulse energy incident on the hook component was 60 uJ (microjoules). This pulse energy was focused through a laser scanner (HPLK XY2026UV, General Scanning, Inc. Arlington, Mass.) to a spot approximately 60 microns in diameter which was scanned over the surface of the component by moving the mirrors with the galvomotors of the scanner. Lines and line segments were created by overlapping the spots created by successive pulses by approximately 50%. The laser pulses were output at 25 kHz and created marked lines at a scanning speed of 0.75 m/s. An image of Example 1 is shown in FIG. 1A.

Example 2

Figure 5:
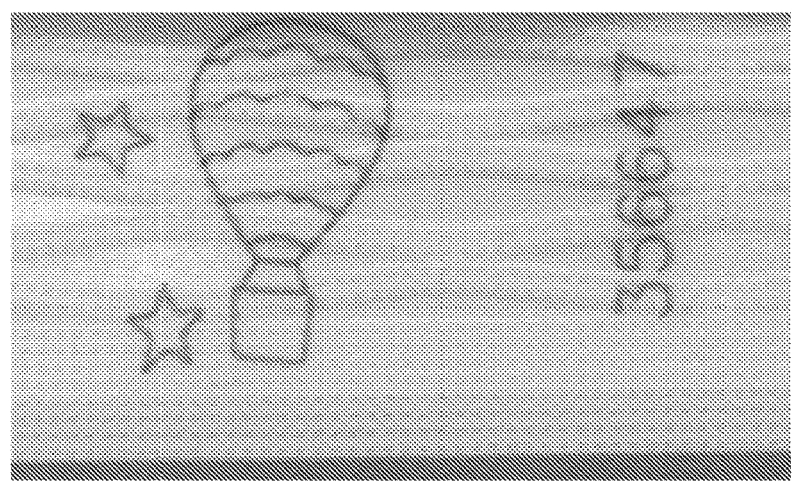
FIG. 5 is a photograph of the printed hook component laminate in Example 2.

Example 2 was a hook laminate composed of a fastening tape and the hook component of Example 1, which was first slit in the machine direction and spread in the cross direction to produce a diamond pattern. The fastening tape was composed of 95.5% polypropylene homopolymer (Fina 3576, Total Petrochemicals, Houston Tex.) and 4.5% (w/w) White 10151005. The film was 82.9 grams per square meter and coated with pressure sensitive adhesive. The diamond-patterned hook component was adhered to the adhesive of the fastening tape. The hook laminate was then marked with a 355 nm laser (Coherent Avia 355-3000, Coherent, Inc. Santa Clara, Calif.). The pulse width of the laser was approximately 40 ns and typical pulse energy incident on the hook laminate was 60 uJ. This pulse energy was focused through a laser scanner (HPLK XY2026UV, General Scanning, Inc. Arlington, Mass.) to a spot approximately 60 microns in diameter which was scanned over the surface of the laminate by moving the mirrors with the galvomotors of the scanner. Lines and line segments were created by overlapping the spots created by successive pulses by approximately 50%. The laser pulses were output at 25 kHz and created marked lines at a scanning speed of 0.75 m/s. An image of Example 2 is shown in FIG. 5.

Example 3

Figure 9:
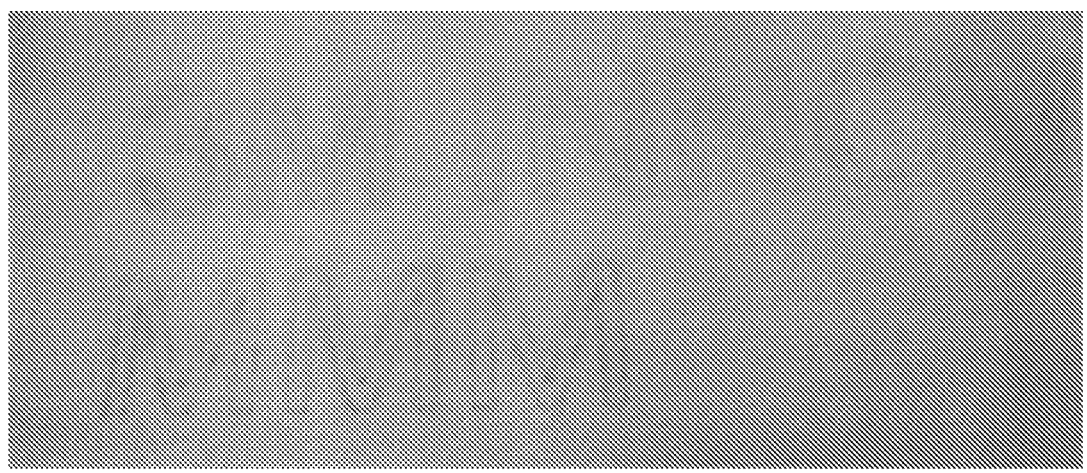
FIG. 9 is a photograph of the printed hook component in Example 3.

Example 3 was a hook component marked with an IR laser. The hook component was composed of 98% Dow C700-35N copolymer, 1% White 1015100S, and 1% (w/w) IR laser additive (LCX 135939 additive masterbatch, RTP Company, Winona, Minn.). The hook component was marked with a 1060 nm laser (SP-40P-HL fiber laser, SPI Lasers UK Limited, Southhampton, UK). The pulse width of the laser was approximately 200 ns and typical pulse energy incident on the hook component was 800 W. This pulse energy was focused through a laser scanner (HurryScan 20 f-theta telecentric lens f=100 mm, Scanlab America, Inc., St. Charles, Ill.) to a spot approximately 50 microns in diameter which was scanned over the surface of the component by moving the mirrors with the galvomotors of the scanner. Lines and line segments were created by overlapping the spots created by successive pulses by approximately 80%. The laser pulses were output at 30 kHz and created marked lines at a scanning speed of 0.3 m/s. An image of Example 3 is shown in FIG. 9.

The embodiments described above and illustrated in the figures are presented by way of example only and are not intended as a limitation upon the concepts and principles of the present invention.

Thus, the disclosure provides, among other things, printed hook components and methods of making the same. Various features and advantages of the printed hook components are set forth in the following claims.

What is claimed is:

1. An article comprising:
   a hook component of a hook-and-loop mechanical fastener, the hook component comprising a first organic polymer and a first metal oxide laser-sensitive agent; and
   a first laser-induced print on the hook component created by the interaction of electromagnetic radiation with the first laser-sensitive agent,
   wherein the hook component has a first side and a second side opposite the first side, and the first laser-induced print is located on either the first or second side of the hook component, and further comprising a second laser induced print on the side of the hook component opposite the side containing the first laser-induced print.

2. The article of claim 1, wherein the first organic polymer is a thermoplastic polymer.

3. The article of claim 1, wherein the first laser-sensitive agent is 0.4% to 8% by weight of the hook component.

4. The article of claim 1, wherein the first laser-induced print comprises at least one of a graphic image, a fiducial mark and a track-and-trace number.

5. The article of claim 1, wherein the hook component is selected from the group consisting of slit, perforated, reticulated, and combinations thereof.

6. The article of claim 1, wherein the hook component comprises a backing having a first side and a second side opposite the first side, and posts extending from the first side of the backing, wherein each post has a proximal end contiguous with the first side of the backing and a distal end opposite the proximal end.

7. The article of claim 6, wherein the distal end of at least some of the posts have shapes selected from the group consisting of mushroom, hook, palm-tree, nail, T, J, and combinations thereof.

8. The article of claim 6, further comprising a carrier laminated to the second side of the backing.

9. The article of claim 8, wherein the carrier comprises a second organic polymer, a second laser-sensitive agent, and a third laser-induced print created by the interaction of electromagnetic radiation with the second laser-sensitive agent.

10. The article of claim 6, further comprising an adhesive on the second side of the backing and a release liner to cover the adhesive.

11. The article of claim 10, wherein the release liner comprises a third organic polymer, a third laser-sensitive agent, and a fourth laser-induced print created by the interaction of electromagnetic radiation with the third laser-sensitive agent.

12. An article comprising:
   a component comprising a first organic polymer and a first metal oxide laser-sensitive agent; and
   a first laser-induced print on the component created by the interaction of electromagnetic radiation with the first laser-sensitive agent
   wherein the component has a first side and a second side opposite the first side, and the first laser-induced print is located on either the first or second side of the component, and further comprising a second laser induced print on the side of the component opposite the side containing the first laser-induced print.

13. The article according to claim 12, wherein the component is selected from the group consisting of a landing zone, a fastening tape, a diaper topsheet and a diaper backsheet.

14. The article according to claim 12, wherein the component comprises a film backing, a nonwoven fabric, a woven fabric and combinations of the aforementioned.

* * * * *